United States Patent [19]

Trombley, III

[11] Patent Number: 4,923,061
[45] Date of Patent: May 8, 1990

[54] CATHETER CURVE RETENTION DEVICE

[75] Inventor: Frederick W. Trombley, III, Billerica, Mass.

[73] Assignee: C. R. Bard, Inc., Murray Hill, N.J.

[21] Appl. No.: 892,128

[22] Filed: Jul. 30, 1986

[51] Int. Cl.⁵ .................. B65D 75/32; B65D 85/02
[52] U.S. Cl. ..................................... 206/364; 206/439
[58] Field of Search .............. 206/364, 363, 349, 438, 206/439, 63.3; 604/280, 281

[56] References Cited

U.S. PATENT DOCUMENTS

| Re. 29,343 | 8/1977 | Amplatz | 604/281 X |
| 3,612,038 | 10/1971 | Halligan | 604/281 X |
| 3,633,758 | 1/1972 | Morse | 206/438 X |
| 3,750,875 | 8/1973 | Juster | 206/364 |
| 3,926,309 | 12/1975 | Center | 206/438 X |
| 3,930,580 | 1/1976 | Bazell et al. | 206/364 X |
| 3,972,418 | 8/1976 | Schuler et al. | 206/63.3 |
| 4,019,633 | 4/1977 | Roth | 206/364 |
| 4,230,115 | 10/1980 | Walz, Jr. et al. | 206/364 X |
| 4,262,800 | 4/1981 | Nethercut | 206/364 |
| 4,537,305 | 8/1985 | Takanashi | 206/438 |

FOREIGN PATENT DOCUMENTS 2223720 5/1972 Fed. Rep. of Germany ...... 206/438

Primary Examiner—Stephen Marcus
Attorney, Agent, or Firm—Wolf, Greenfield & Sacks

[57] ABSTRACT

A retaining device for receiving the curved distal end of a catheter to maintain the catheter in its curved configuration and to prevent straightening of the curved catheter is formed from a pair of flexible sheets face-to-face and sealed to each other along a line conforming to the periphery of the curve of the catheter, the pocket having an opening therein to receive the curved distal end of the catheter. The sheets are permeable to sterilizing agent and may be torn apart to separate them and permit easy removal of the catheter when the catheter is to be used.

9 Claims, 1 Drawing Sheet

CATHETER CURVE RETENTION DEVICE

FIELD OF THE INVENTION

This invention relates to improvements in techniques and devices to maintain the curvature of the distal end of a catheter in its predetermined curved configuration until the catheter is to be used.

BACKGROUND OF THE INVENTION

This invention relates to techniques for retaining catheters such as angiographic and coronary catheters so as to maintain their shape during sterilization and shelf life. More particularly, the invention relates to a packaging device to retain the curved end of the catheter and to prevent it from losing its predetermined curved shape during sterilization, storage and handling. Thus, the invention serves to maintain the shape of the catheter until the catheter is ready for use in its intended procedure.

Physicians use a wide variety of catheters for numerous procedures. Many types of catheters, such as angiographic and coronary catheters, are formed with a wide variety of special curves at their distal ends and are adapted for different procedures. The curves typically are designed specifically to facilitate manipulation and location of the distal end of the catheter precisely at the intended location in accordance with the particular procedure to be performed.

Among the difficulties presented with such catheters is that the curves tend to straighten out from the time the catheter is manufactured until the time it is actually put in use. A change in the configuration of the curve often will render the catheter unusable for the intended procedure. The catheters typically are formed from a urethane material and are manufactured to include the desired special curve at the distal end. Typically they are packaged after manufacture and the package is exposed to a sterilization procedure which includes the application of heat. The elevated temperatures cause the urethane material to relax from its curved shape to a more straightened configuration. Additionally the curved ends of the catheter tend to straighten out somewhat over time even at ambient temperatures.

In order to maintain the distal end of the catheter in its predetermined curve, it has become the practice to package the catheter in a special plastic tray having various slots and grooves intended to receive and grip the catheter, especially at its curved distal end to securely retain the distal end in its predetermined curve. By way of example, U.S. Pat. No. 3,839,841 to Amplatz discloses such a catheter tray. U.S. Pat. No. 3,633,758 to Morse discloses still another type of catheter storage rack for retaining a catheter at its curved distal end at its predetermined configuration. Such trays and devices are somewhat cumbersome and can be costly. It is among the general objects of the invention to provide a low cost simple device for retaining the curved end of a catheter in its predetermined curved shape.

SUMMARY OF THE INVENTION

The present invention employs a pair of thin film parallel sheets arranged to define a pocket having an open end adapted to receive the curved distal end of the catheter. The sheets, which may be formed from a suitable plastic are sealed to each other at predetermined locations to define the pocket. The periphery defined by the pocket is arranged to permit the curved distal end of the catheter to be inserted into the pocket but to resist easy withdrawal of the cateter. The sealed locations are selected so that they will engage the distal end of the catheter at locations arranged to prevent the curved distal end of the catheter from straightening out. With the distal end of the catheter inserted into the pocket, any tendency of the catheter to relax to a straightened configuration from the predetermined curve is restrained by the sealed segments. The device is formed so that the sheets have flaps extending peripherally beyond the sealed segments by which the sheets may be gripped and pulled apart to expose the distal end of the catheter for use. The catheter, fitted with the curve retention device may be packaged in any of a number of conventional containers or catheter trays.

It is among the general objects of the invention to provide a device for retaining the curved distal end of a catheter in its curved configuration during sterilization and during its shelf life until the catheter is ready for use.

A further object of the invention is to provide a device of the type described which is of low cost, simple construction.

A further object of the invention is to provide a device of the type described which will maintain its shape and form during sterilization procedures.

DESCRIPTION OF THE DRAWINGS

The foregoing and other objects and advantages of the invention will be appreciated more fully from the following further description thereof with reference to the accompanying drawings wherein.

DESCRIPTION OF THE PREFERRED EMBODIMENT

Figure 1:
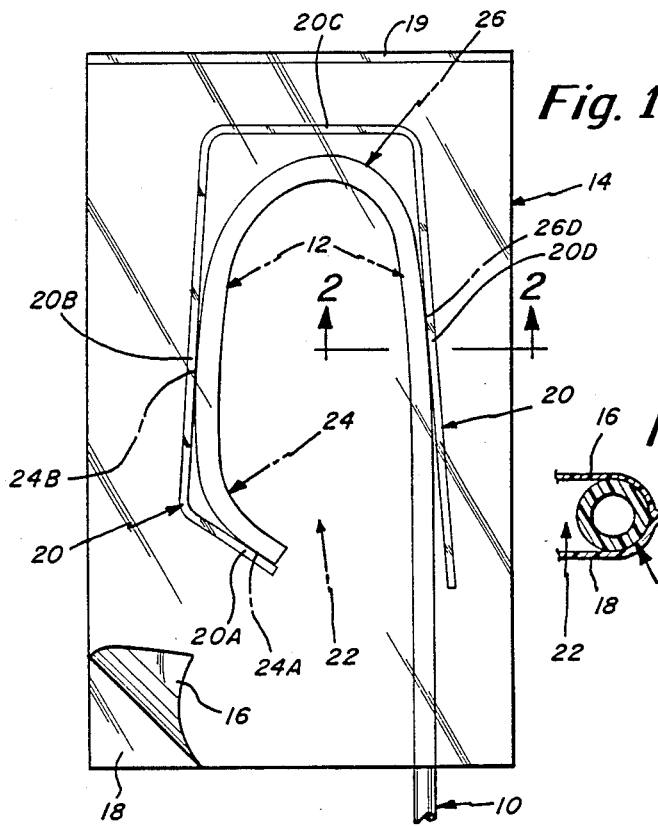
FIG. 1 is a plan view of one type of catheter having a Judkins left curved distal end and contained within the retention device of the invention.
Figure 2:
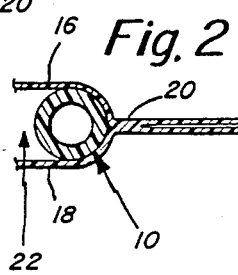
FIG. 2 is a sectional illustration of the invention as seen along the line 2—2 of FIG. 1.

FIG. 1 of the drawings illustrates a coronary catheter 10 having a curved distal end 12, the particular curve shown lying substantially in a plane and being known as the Judkins left curve. As described above, the catheter typically is formed from materials and in a manner such that when subjected to heat, handling or long term storage the curves in the catheter may tend to relax to a more straightened configuration.

In accordance with the present invention the curves are retained in the distal end of the catheter by a retention device indicated generally at the reference character 14. The retention device is formed from a pair of thin, flexible sheets 16, 18. The sheets 16, 18 preferably are formed from a thin film of plastic material, such as polyethylene, which can be heat sealed easily. The sheets 16, 18 may be preliminary attached along one margin as indicated at 19 to facilitate handling of the sheets 16, 18 together. The sheets 16, 18 are attached to each other, as by heat sealing, along one or more lines or points, indicated generally at 20, located at critical locations about the curved distal end 12 of the catheter 10. The lines or points 20 are formed to define at least one interruption 22 which defines an opening through which the curved distal end 12 of the catheter may be inserted. The lines 20 thus define a pocket having a peripheral shape adapted to receive the catheter tip in a manner which will prevent the curved catheter tip from relaxing to a straightened shape either from exposure to heat or with the passage of time.

It is not necessary that the lines 20 which define the periphery of the pocket parallel precisely the shape of the catheter curve. It is only necessary that the lines 20 be located to engage the catheter at selected points along the curved tip which will restrain the curves in the distal tip from relaxing to a straightened configuration. Thus, as shown in FIG. 1, the Judkins left curve can be maintained with a pocket having a periphery defined by a line 20 which bears merely a general resemblance to the shape of the Judkins curve. In order to retain the curves on the catheter, the pocket-defining line 20 should be formed to engage the catheter on at least one point near proximally and distally of each curve. For example, in the Judkins left configuration shown in FIG. 1, the most distal primary curve 24 is engaged at a point located distally of the curve 24 by the segment 20A of the line 20. Segment 20B of the line 20 is oriented to engage a point of the catheter proximally of the primary curve 24. Thus, segments 20A and 20B engage, respectively, points 24A and 24B on the catheter and will prevent the primary curve 24 from straightening out. Similarly, the secondary curve 26 in the catheter is prevented from straightening out by engagement of the catheter at a point 26D on the proximal side of the secondary curve 26 as well as engagement at the point 24B on the distal side of the secondary curve 26. It may be noted that in this embodiment, where there are a series of at least two curves, the engagement of the line segment 20B with the point 24B on the catheter curve serves to cooperate to maintain both the primary curve 24 and secondary curve 26 of the catheter in their curved configurations. It may be noted further, that although line segment 20C is not illustrated as engaging any part of the distal end of the catheter, it does serve further to define the pocket in which the distal end of the catheter is received. In that regard, the line 20 which defines the peripheral configuration of the pocket, should be arranged to retard dislodgement of the retention device 14 from the catheter in normal handling and use, although it need not be configured so as to so completely enclose the curve as to render it impossible to pull the device 14 off of the catheter. In that regard, the pocket should be configured to permit the catheter to be inserted into the pocket through the opening defined as 22 in the embodiment shown in FIG. 1.

Figure 3:
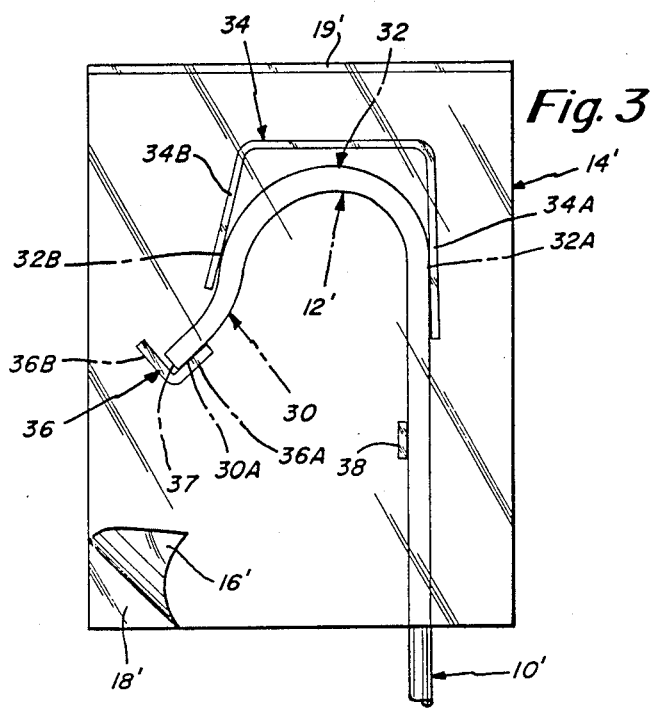
FIG. 3 is a plan view of another type of catheter, having an Amplatz curve at its distal end and contained within a retention device in accordance with the invention.

FIG. 3 illustrates another catheter curve, known as the Amplatz curve and a retention device 14' for use with the Amplatz curve. The Amplatz curve is characterized by a primary curve 30 and a secondary curve 32 which curves in a reverse direction from the primary curve 30. The Amplatz configuration of reverse primary and secondary curves 30, 32 sometimes is referred to as a "Shepard's crook" curve. The retention device used with the Amplatz curve illustrates that the attached regions of the sheets 16', 18' need not be continuous and may define an interrupted pattern of lines, points and segments. Thus, in the embodiment shown in FIG. 3, the secondary curve 32 is retained by means of an attachment line 34 having segments 34A and 34B which engage the catheter proximally and distally of the secondary curve 32 at the points 32A, 32B. The primary curve 30 is retained by an L-shaped line of attachment 36 which has a segment 36A which engages the catheter at a location 30A which is distal of the primary curve 30. Thus, the configuration of the primary curve 30 is retained by engagement of the catheter proximally of the curve 30 (at point 32B) and distally of the curve 30 (at point 30A). Thus, in this embodiment attachment line segment 34B serves as a common segment to aid in retaining both primary and secondary curves 30, 32 in their curved configuration. As is the case in connection with the embodiment illustrated in FIG. 1, the retention device 14' illustrated in FIG. 3 will tend to retain the primary and secondary curves and will prevent them from relaxing to a straightened configuration from exposure to heat or an extended shelf life.

In the embodiment illustrated in FIG. 3, the attachment line 36 also includes a segment 36B which faces the distal outlet tip of the catheter. Segment 36B prevents the retention device 14' from easily slipping off the catheter in a direction which parallels the distal-most tip portion of the catheter, extending from the primary curve 30 to the distal tip 37 of the catheter. The embodiment in FIG. 3, used with the Amplatz curve, also includes another attachment point 38 which further serves to retain the retention device 14' on the catheter.

In each embodiment of the invention, the attachment lines, points or segments, as appropriate, are located and configured both to provide resistance points at selected locations on opposite sides of each of the curves in the catheter as well as to prevent the retention device from easily separating from the catheter while also permitting the retention device to be slipped onto the distal end of the catheter.

The sheets 16, 18 preferably are provided with peripherally extending margins or flaps by which the sheets 16, 18 may be gripped and pulled apart when the catheter is to be used. The peripherally extending margins or flaps are defined inherently about the attachment lines when the sheets 16, 18 are attached by forming the attachment lines within the peripheral confines of the sheets 16, 18. In each of FIGS. 1 and 3, the margins are illustrated as being separated in the lower left-hand corners of the device from which it may be seen that continued pulling apart of the margins will separate the sheets 16, 18 at the attachment lines thus fully opening the pocket and permitting the catheter to be removed.

Figure 4:
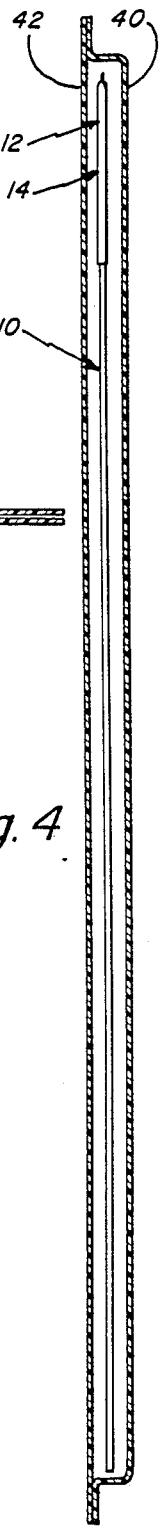
FIG. 4 is a side elevation, partly in section, of the catheter with the curve retention device contained in a sealed package.

After the catheter has been formed and its distal end inserted into the retention device 14, the catheter, with retention device 14 attached may be packaged in any of a wide variety of conventional packages or envelopes used to package such catheters. FIG. 4 illustrates diagrammatically and in section a catheter with a retention device enclosed within a package. The package typically may include a formed plastic tray 40 covered by a thin plastic film 42 which is sealed to the tray by any conventional means, such as by heat sealing. The catheter, so packaged, then is exposed to a sterilization procedure, such as by exposure to an ethylene oxide under heat and pressure. The materials used in the outer package as well as the material for the retention device 14 are permeable to the sterilizing agent. During sterilization, any tendency for the catheter curve to relax and straighten out under the influence of the heat to which it is exposed is restrained by the points of engagement of the retention device 14. When the catheter cools back to room temperature it will have been retained in its curved configuration and thus will retain its predetermined shape.

By way of example, the sheets 16, 18 may be formed from extruded polyethylene sheet of the order of 0.0025" thickness and can be heat sealed along the attachment lines and segments. The material must be permeable to sterilizing agents such as ethylene oxide and should be dimensionally stable throughout the range of temperatures to which the device will be exposed, as during sterilization so that it will not relax under the conditions it will encounter, such as sterilization. Typically, temperatures achieved during sterilization are of the order of 100°–140° F. It should be understood, however, that other materials for the sheets may be employed. For example, one or both of the sheets may be formed from other plastic materials or from paper suitably treated to withstand the environments of sterilization and shelf life and adhesively attached to each other along the attachment lines. Paper coated with heat sealable films such as polyethylene also may be employed. Composite retention devices also may be employed in which one sheet is paper and the other a transparent plastic.

From the foregoing, it will be appreciated that the invention provides a low cost simple and easily manufactured retention device for catheters having curved distal end and, particularly, catheter configurations in which the curved distal ends lie substantially in a plane. It should be understood, however, that the foregoing description of the invention is intended merely to be illustrative thereof and that other embodiments and modifications may be apparent to those skilled in the art without departing from its spirit.

Having thus described the invention, what I desire to claim and secure by letters patent is:

1. In combination, a catheter having a preformed curved distal end and a device for retaining the preformed curved distal end of the catheter in its preformed curved configuration comprising:
   said distal end of said catheter having at least one preformed curve formed therein;
   said retention device comprising a pocket receptive to the preformed curved distal end of the catheter, said locations being disposed to restrain said curve in the curved distal end of the catheter at at least one point proximally and distally of the curve;
   said pocket having an opening adapted to enable the preformed curved distal end of the catheter to be inserted into the pocket;
   said distal end of the catheter being received in the pocket.

2. A catheter and retention device as defined in claim 1 further comprising:
   the sheets having flaps extending peripherally of the pocket, said flaps being adapted to be gripped to enable the sheets to be torn apart.

3. A catheter and retention device as defined in claim 1 wherein the facing surfaces of the sheets are formed from a thermoplastic material and are heat sealed to each other at said locations.

4. A catheter and retention device as defined in claim 3 wherein the sheets are formed from a polyethylene.

5. A catheter and retention device as defined in claim 1 wherein at least one of the sheets is formed from a material which is permeable to ethylene oxide.

6. A catheter and retention device as defined in claim 1 wherein the sheets and means for attaching the sheets to each other is selected to withstand temperatures as great as the order of 140°.

7. A catheter and retention device as defined in claim 1 wherein the pocket is substantially planar said catheter having a curved distal end which lies substantially in a plane.

8. A catheter and retention device as defined in claim 1 wherein the pocket is formed to define a configuration adapted to resist removal of the curved end of the catheter through the opening in the pocket.

9. A catheter and retention device as defined in claim 1 further comprising:
   said pocket being shaped to conform to the periphery of the curved distal end of the catheter.

* * * * *

UNITED STATES PATENT AND TRADEMARK OFFICE
CERTIFICATE OF CORRECTION

PATENT NO. : 4,923,061
DATED : May 8, 1990
INVENTOR(S) : Frederick W. Trombley, III It is certified that error appears in the above-identified patent and that said Letters Patent is hereby corrected as shown below:

Col. 6, line 3, after "comprising" insert --a pair of sheets arranged face-to-face and having facing surfaces attached to each other at locations to define --.

Signed and Sealed this

Sixteenth Day of August, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 4,923,061
DATED : May 8, 1990
INVENTOR(S) : Frederick W. Trombley, III It is certified that error appears in the above-indentified patent and that said Letters Patent is hereby corrected as shown below:

In Column 6, Claim 1, Line 3, after "a", insert -- pair of sheets aranged face to face and having facing surfaces attached to each other at locations to define a --

This certificate supersedes Certificate of Correction issued August 16, 1994.

Signed and Sealed this

Twenty-fourth Day of January, 1995

Attest:

BRUCE LEHMAN

Attesting Officer

Commissioner of Patents and Trademarks